United States Patent [19]

Murray

[11] Patent Number: 6,051,435

[45] Date of Patent: Apr. 18, 2000

[54] METHOD FOR DETECTING GROWTH STRESS IN PLANTS

[75] Inventor: Allen K. Murray, Newport Beach, Calif.

[73] Assignee: Glycozyme, Inc., Irvine, Calif.

[21] Appl. No.: 09/003,679

[22] Filed: Jan. 7, 1998

Related U.S. Application Data

[63] Continuation-in-part of application No. 08/516,953, Aug. 18, 1995, Pat. No. 5,710,047.

[51] Int. Cl.⁷ .................................................. G01N 33/68

[52] U.S. Cl. .................................. 436/94; 436/174; 47/58

[58] Field of Search ............................. 436/94, 174, 161; 47/58

[56] References Cited

U.S. PATENT DOCUMENTS 5,710,047  1/1998  Murray ........................................ 436/94

*Primary Examiner*—Lyle A. Alexander
*Attorney, Agent, or Firm*—Graham & James LLP

[57] ABSTRACT

A method of detecting environmental stress in plants, particular water stress in cotton plants is based on a hot dilute acid extraction of plant tissues such as cotton fibers. The extracts are analyzed by high pH anion exchange chromatography to separate and characterize the carbohydrates. This method extracts a characteristic series of carbohydrate multimers containing galactose, mannose and glucose. The pattern of multimers is indicative of growth stress during the formation of the plant tissue. In addition, similar multimers can be extracted from textiles and are indicative of textile wear and can be used to determine which manufacturing treatment will improve fabric life.

1 Claim, 17 Drawing Sheets

METHOD FOR DETECTING GROWTH STRESS IN PLANTS

The present application is a Continuation In Part of application Ser. No. 08/516,953, filed on Aug. 18, 1995, and now issued as U.S. Pat. No. 5,710,047 which is hereby incorporated by reference into this application.

BACKGROUND OF THE INVENTION

1. Field of the Invention

This invention concerns a method of detecting environmental stress in green land plants, particularly in agricultural crops, so that production can be optimized by alleviating the stress before permanent damage to the plants occurs. In particular this application describes biochemical methods of assessing quality of cotton fibers.

2. Description of Related Art

In the parent of this application the present inventor described his surprising discovery that it was possible to extract a carbohydrate-containing fraction from properly prepared plant material by a simple cold water process. Essentially, plant tissue is prepared by rapid freezing (preferably by use of liquid nitrogen or solid carbon dioxide) and is then lyophilized and stored at temperatures below freezing. As disclosed in the above-referenced parent application carbohydrate-containing cell wall fractions can be easily extracted from the lyophilized tissue by cold aqueous extraction; then, greatly improved techniques of High Pressure Liquid Chromatography (HPLC) allow resolution of the aqueous extract into constituent mono and polysaccharides which can be further hydrolyzed to identify the constituent monosaccharides.

The use of high pH anion exchange chromatography (HPAEC) makes possible the unambiguous identification of cell wall constituents. In HPAEC a salt gradient (such as a sodium acetate gradient) is applied to a column of special ion exchange resins held at a high pH to sequentially elute various mono and polysaccharides. Essentially, the hydroxyl groups of the sugars act as extremely weak acids which become deprotonated at the high pH, binding to the ion exchange matrix until eluted by the gradient.

While there are a number of vendors of HPAEC materials, the current invention has employed products and systems produced by the Dionex Corporation of Sunnyvale, Calif. These products and systems are explained in full in the Dionex Technical Notes, particularly in Technical Notes 20 and 21, which are hereby incorporated into this application. The carbohydrate fractions isolated from plant cell walls were analyzed using Dionex CarboPac PA1 and PA-100 columns. Both of these columns contain poly-styrene/divinylbenzene cross-linked latex microbeads (350 nm diameter) with quaternary amine functional groups. The columns were operated under the manufacturer's recommended pressure conditions (4000 psi maximum) in sodium hydroxide eluted with a sodium acetate elution gradient. When necessary, sugar alcohols were analyzed using a CarboPac MA1 column which contains porous beads (8.5 $\mu$m diameter) of vinylbenzene chloride/divinylbenzene with alkyl quaternary ammonium functional groups.

The polysaccharides analyzed in the present invention are appropriately referred to as "glycoconjugates" because they comprise a monosaccharide conjugated to at least one additional monosaccharide (i.e., to form an oligo or polysaccharide) and optionally to a protein or a lipid. As will be disclosed below at least some of the glycoconjugates comprise polysaccharides conjugated to a protein moiety. To summarize glycoconjugates may be polysaccharides, polysaccharides containing a protein moiety, polysaccharides containing a lipid moiety and/or any combination of these. In the present application only polysaccharides and polysaccharides containing a protein moiety have been unambiguously identified. In any case HPAEC characterizes the polysaccharide component of the glycoconjugate.

In the parent application two groupings of polysaccharides were especially pointed out and described by their position in HPAEC separations; these groups were identified as GC-1 and GC-2. Herein the composition of these groupings is further elucidated and other important polysaccharides (glycoconjugates) are discussed.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Figure 1:
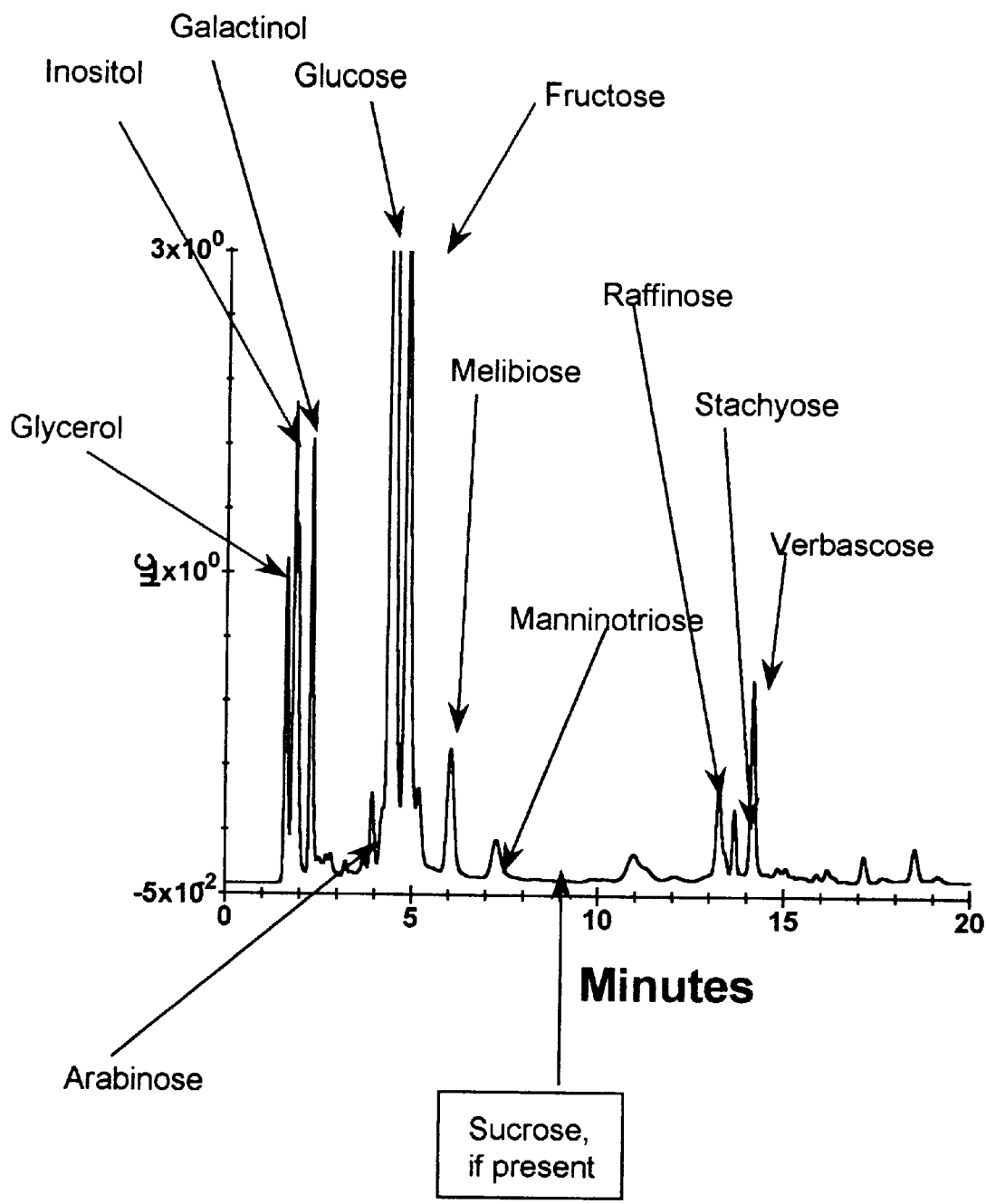
FIG. 1 shows an HPAEC of a cold aqueous extract of cotton fibers according to the present invention indicating the position and identity of a number of carbohydrates.

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide methods for determining plant growth stress and the quality of plant materials, especially cotton fibers, through the analysis of certain polysaccharide fractions.

As already discussed, glycoconjugates are carbohydrates covalently linked to other carbohydrates, proteins or lipids. The glycoconjugates monitored in the present study appear to function as cell wall precursors or intermediates in the biosynthetic processes that produce the cell wall. Cotton fibers are unique as plant cells in that their primary function is the synthesis of cell wall material. A progression of appearance and disappearance of specific glycoconjugates has been observed in developing cotton fibers under "normal" conditions. Developing cotton fibers obtained from plants subjected to various forms of stress, which negatively impacted fiber development, demonstrate an abnormal or altered pattern of appearance and disappearance of the glycoconjugates monitored. Glycoconjugate analysis is a sensitive method of monitoring cell wall synthesis which is directly coupled with cell growth. This analysis is applicable to roots, stems, leaves and fruits. In the present case, the analysis has been applied to a fruit. The presence of these glycoconjugates has been demonstrated in a range of different plants which leads to the conclusion that they will be found in virtually all plant cells. In addition to the monitoring of fiber growth and development, glycoconjugate analysis will demonstrate the presence of trehalulose or melizitose, oligosaccharides present in whitefly honeydew, if they are present. Thus, the method is also useful for monitoring insect pests.

Sucrosyl Oligosaccharides (GC1 Glycoconjugates)

The GC-1 series of glycoconjugates described in detail in the parent application is shown here to be composed of molecules in the raffinose series of oligosaccharides also known as the sucrosyl oligosaccharides. Raffinose is a nonreducing trisaccharide consisting of D-galactose, D-glucose and D-fructose with the galactose and glucose linked by an α-1,6 glycosidic bond, and the fructose linked to the glucose by an α, β-1,2-glycosidic bond. That is, raffinose comprises a galactose unit linked to sucrose (glucose+fructose). It is believed that raffinose is synthesized by transferring a galactose unit from galactinol (dulcitol) to sucrose. Galactinol is produced by transferring a galactose unit from UDP-galactose to myo-inositol. Successive members of the raffinose series (stachyose, verbascose, and higher homologs) are produced by stepwise addition of galactose units. Thus, stachyose has two galactose units (galactobiose) added to sucrose, and verbascose has three, etc. At each step a galactinol molecule yields one galactose unit and one free myo-inositol molecule. Related sugars include melibiose (galactose+glucose) and manninotriose (galactose+galactose+glucose).

Until now the majority of research on the sucrosyl oligosaccharides has focused on their synthesis and apparent role as storage products in seeds. However, it is likely that these oligosaccharides serve as glycosyl donors for polysaccharide synthesis in cell walls (e.g., cotton fibers). There is a large body of literature describing cell wall invertases in a wide variety of plants. However, no obvious function for cell wall invertases has been proposed other than for cells in suspension culture. One report of the invertases in developing cotton fibers (Bucala, 1987) compared the activity of the cell wall invertases on sucrose, raffinose and stachyose. As might be expected from kinetic considerations, the activity decreased with increasing molecular weight. It seems likely that the cell wall (insoluble) invertases are cleaving fructose from the raffinose series compounds and transferring these sugars to other carbohydrates that comprise part of the complex cell wall structure. In one experiment it was possible to verify that the insoluble invertases convert verbascose (galactose, galactose, galactose, sucrose) to verbascotetrose (galactose, galactose, galactose, glucose). Presumably the cleaved fructose is added to some other carbohydrate.

Figure 2:
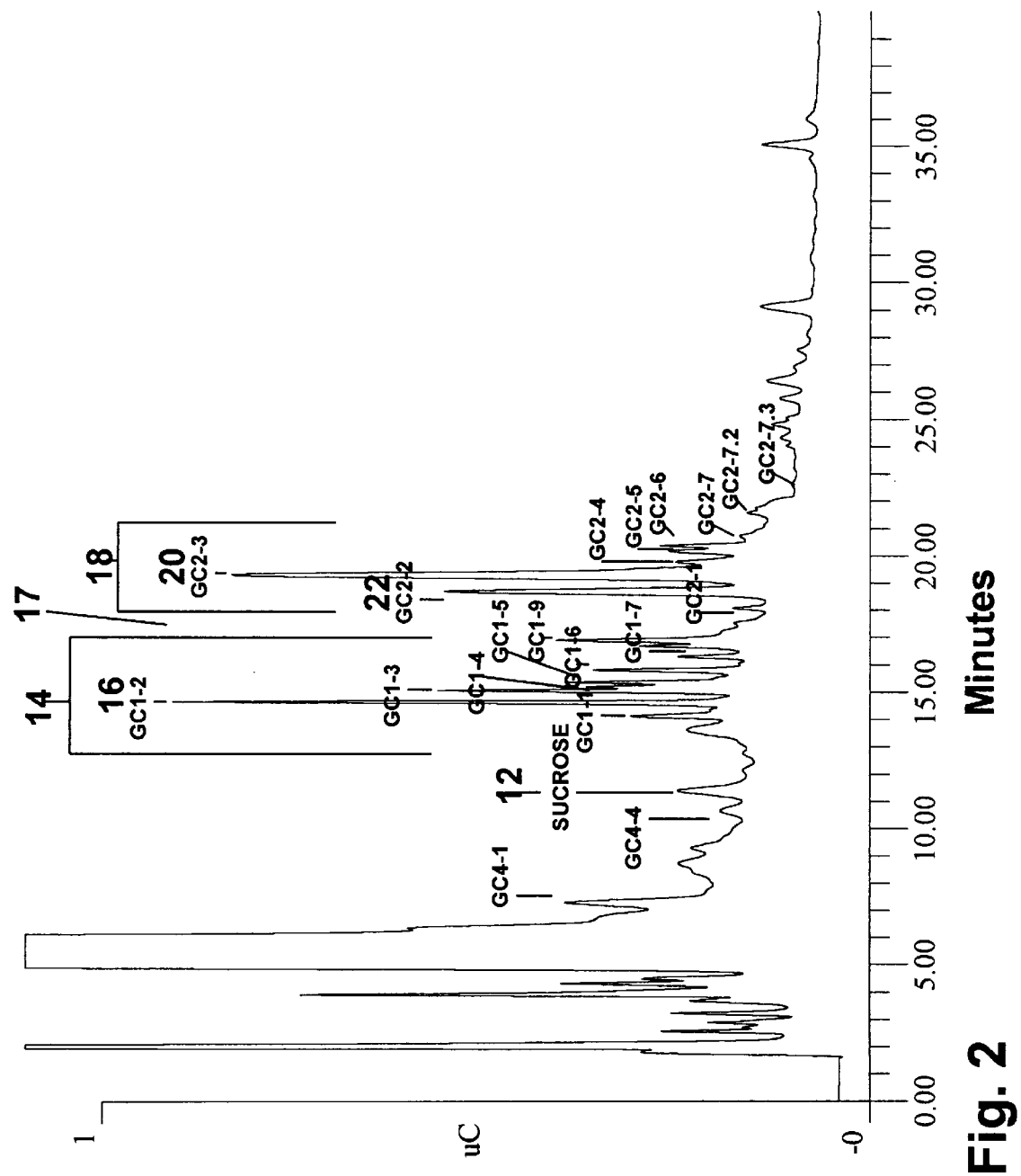
FIG. 2 shows a typical HPAEC cold aqueous extract to show the position of the GC-1 and GC-2 carbohydrates.

Earlier GC-1 compounds (14) in FIG. 2 were defined as a group of carbohydrates that run at around 15 minutes in the standard separations described in the standard separations disclosed in the parent application. FIG. 1 shows a portion of a chromatogram similar to that of FIG. 2 except that the various carbohydrate peaks have been identified through hydrolysis experiments and through running known standards. Significantly the GC-1 compounds are identified as raffinose, stachyose and verbascose. Preliminary results indicate that samples with additional GC-1 peaks (e.g., FIG. 2) have additional higher homologs of the raffinose series. The significant point is that "raffinose series carbohydrates" is a more accurate term that can be substituted for GC-1 carbohydrates in the methods of the parent application. From quantitative interrelationships shown in the parent application GC-1 carbohydrates are believed to be precursors to the GC-2 carbohydrates. However, whereas raffinose series carbohydrates are nonreducing, current experiments have shown that the GC-2 carbohydrates are reducing. Thus, GC-1 compounds are probably not directly converted into GC-2 compounds. Rather carbohydrates are probably transferred (perhaps by the agency of a cell wall invertase) to other carbohydrate molecules to form GC-2 compounds.

Figure 4:
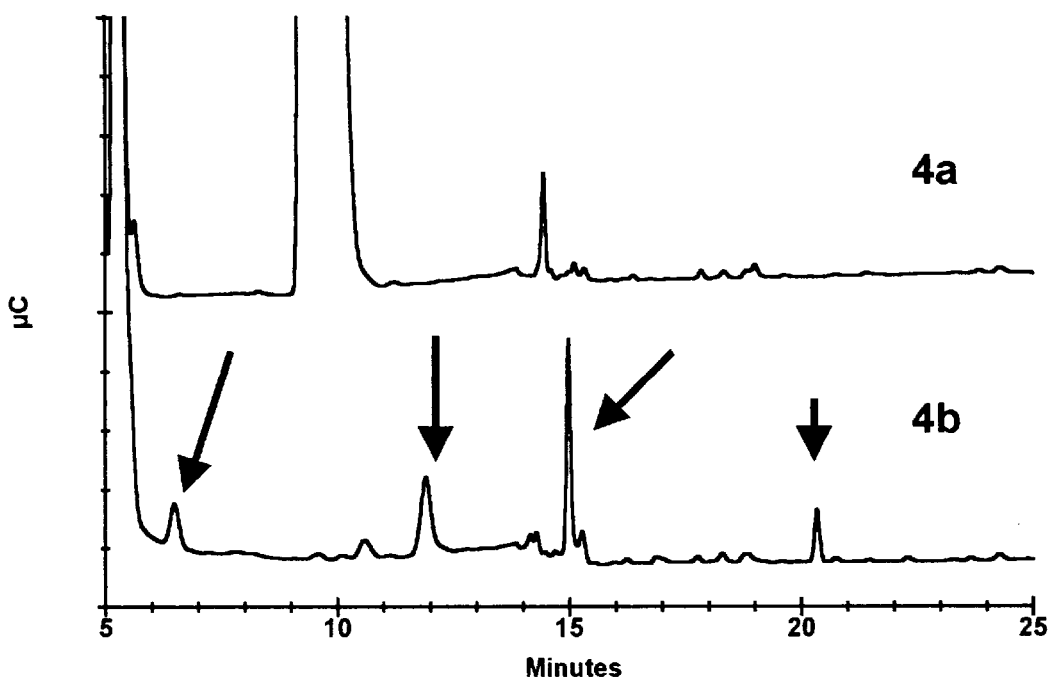
FIG. 4 shows the effect of incubating the cold aqueous extract with normally grown fibers wherein insoluble enzymes cause changes in the carbohydrate profile (arrows); the control uses fibers boiled to destroy the enzymes.
Figure 5:
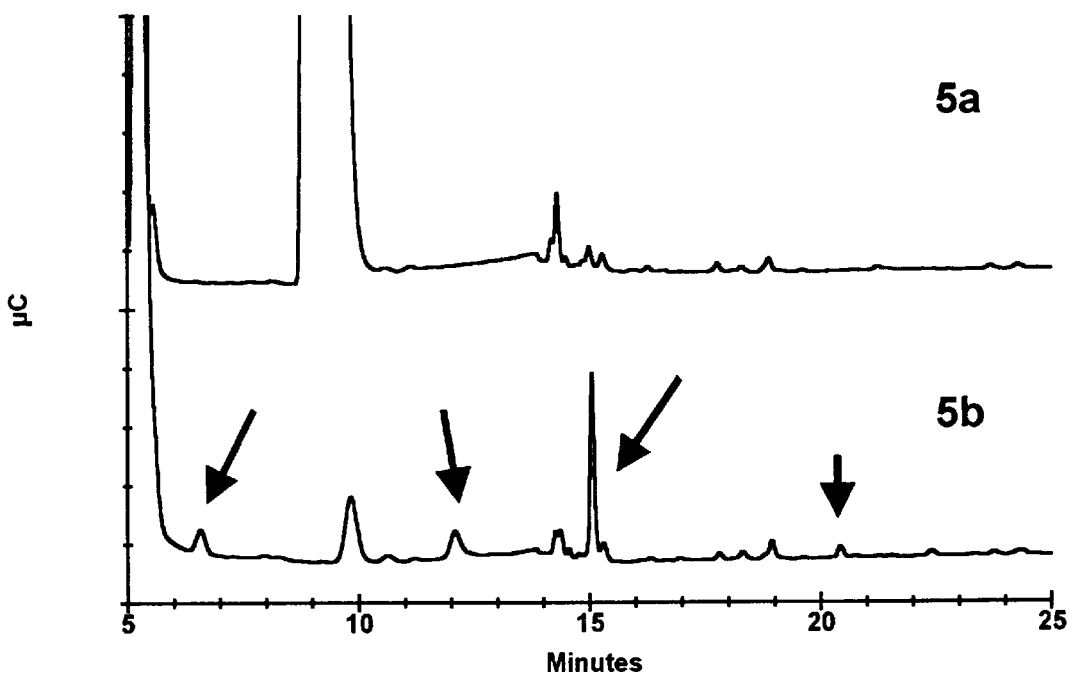
FIG. 5 shows the effect of incubating the cold aqueous extract with drought grown (no irrigation) fibers wherein insoluble enzymes cause changes in the carbohydrate profile (arrows); the control uses fibers boiled to destroy the enzymes.

An extremely exciting and unexpected discovery of the present study is that the synthetic enzymes necessary to make the GC-1 to GC-2 interconversions (and presumably other steps of cell wall synthesis) are preserved by lyophilization. If the cold aqueous extract is allowed to react with the fibers (which contain the nonsoluble enzymes), the carbohydrate profile of the extract changes with time as simple sugars are used up and more complex carbohydrates appear in their place. FIG. 4 shows the results of incubating a cold aqueous extract of normally grown cotton with the fibers from which the extract was made. FIG. 4a shows the control (i.e., the aqueous extract) while FIG. 4b shows the results of the incubation in which the aqueous extract was added back to the fibers and incubated for 1 hr at 37° C. Note the disappearance of the carbohydrate at the ten minute point and the appearance of several new carbohydrates. Those at around 15 minutes are GC-1 compounds and those around 20 minutes are GC-2 compounds. If the aqueous extract is boiled prior to being added back to the fibers, the results are unchanged. If the fibers are boiled prior to the incubation, there is no change in the carbohydrates during the incubation. This clearly shows that the reaction is driven by insoluble enzymes in the fibers. If the fibers are dried and weighed following the incubation a significant increase in weight is detected. This shows that insoluble carbohydrates are added to the fibers (i.e., to the cell walls); the changes seen in the soluble carbohydrates are probably simply incidental to the cell wall additions. FIG. 5 shows a similar experiment carried out using fibers from nonirrigated plants that were undergoing drought stress. The parent application demonstrates that GC-1 and GC-2 compounds are sensitive indicators of stress. Here we see that these differences are also demonstrated by the in vitro incubation experiments.

Figure 6:
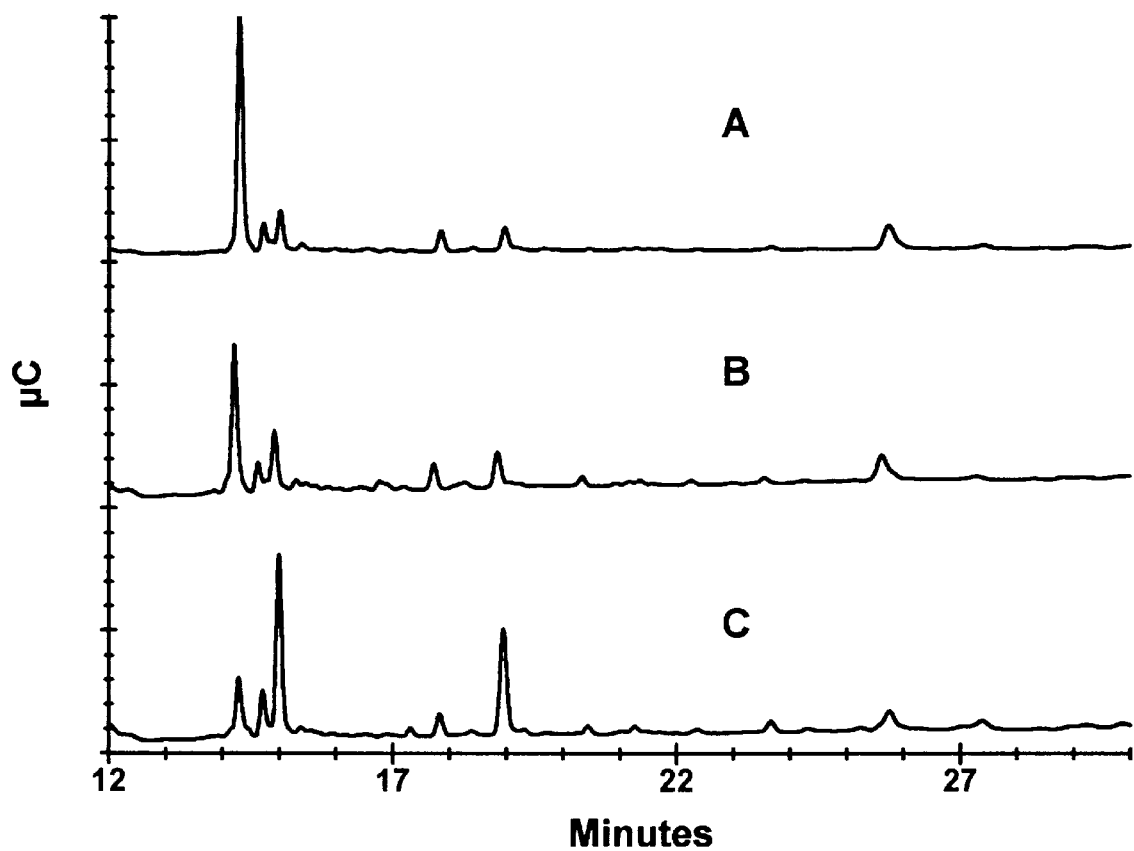
FIG. 6 shows cold aqueous extracts from fibers taken at different times of day (early [A], mid [B], and late [C]) to illustrate that the carbohydrate pattern varies predictably with time of day.

One might ask whether the drought stress differences are due to changes in the insoluble enzymes, changes in the availability of carbohydrate precursors or both. It is well-known that carbohydrates are involved in drought response of stressed plants. For example, glycerol or trehalose may accumulate in response to drought and act as protective agents to maintain cell and membrane integrity. Clearly if carbohydrates are diverted to produce protective materials, the carbohydrate pool available for cell wall synthesis may be altered. The present study has also demonstrated that the carbohydrate patterns fluctuates during the day as the rate of photosynthesis increases (early to mid day) and then decreases (mid to late day). This is demonstrated in FIG. 6 which shows the aqueous extracts taken from fibers harvested at three different times of day (early, within one hour of dawn; mid, within one hour of noon; and late, within one hour of dusk). Of course, the activities of various cell wall enzymes might also vary during the day, thereby further complicating the picture.

The likelihood that stress changes in cell wall carbohydrates is due to carbohydrate pool shifts rather than changes in wall enzymes has also been demonstrated by combining aqueous extracts of normal fibers with fibers from drought stressed plants and vice versa. In either case the resulting profiles are largely controlled by the source of the extract. That is, extracts from normally grown fibers give essentially normal profiles when incubated with fibers either from normal or stressed plants. Similarly, extracts from stressed plants give abnormal profiles when incubated with fibers from either normal or stressed plants. However, adding known substrates to the normal or stressed fibers gives some indication that the fibers also control the final soluble carbohydrate profiles.

Figure 7:
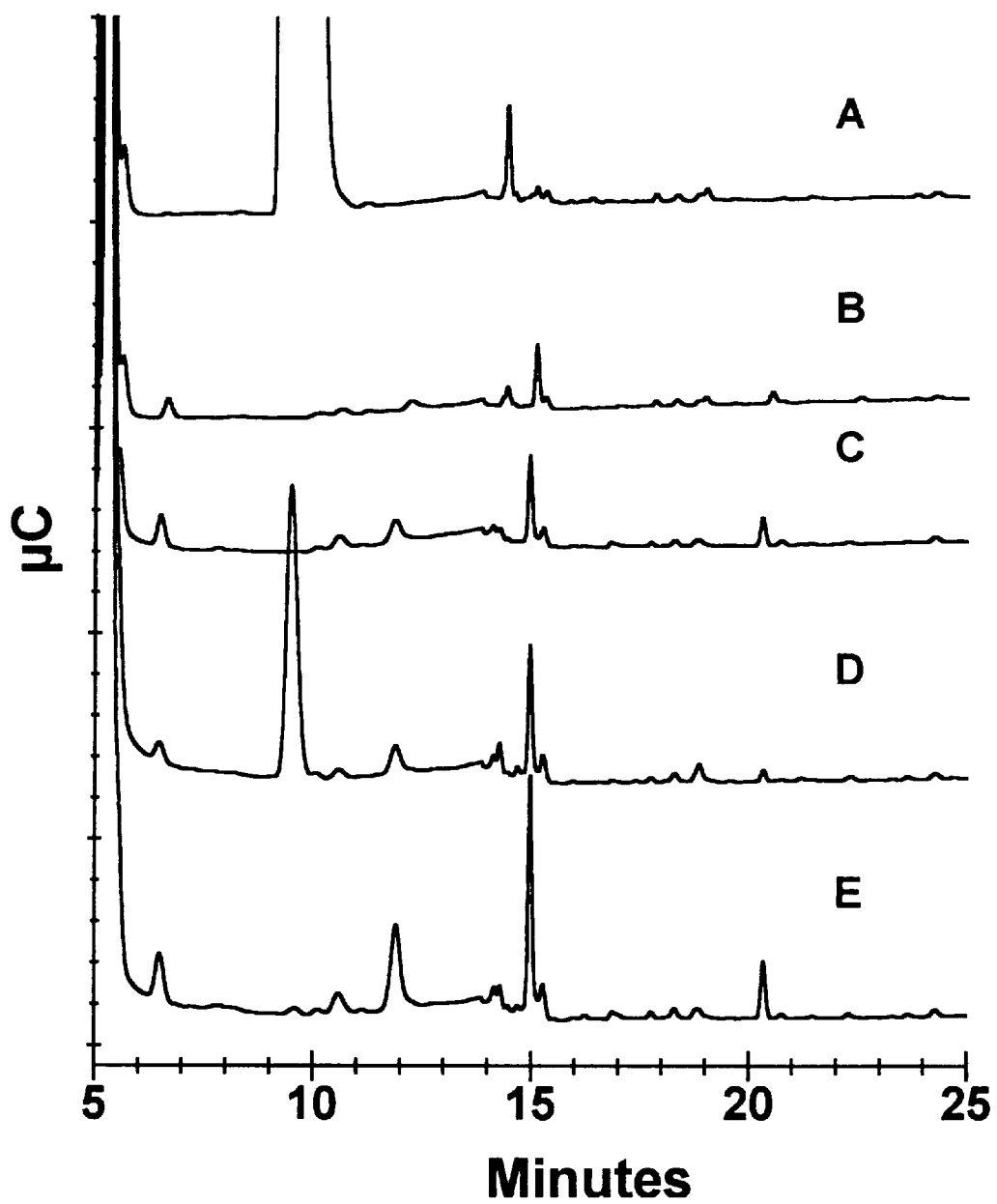
FIG. 7 shows the effect on the carbohydrate profile of incubating normally grown cotton fibers (harvested according to the method of the invention) with a number of different added substrates: A) control-boiled to destroy enzymes; B) inositol added; C) glycerol added; D) sucrose added; and E) inositol, glycerol, sucrose and arabinose added.
Figure 8:
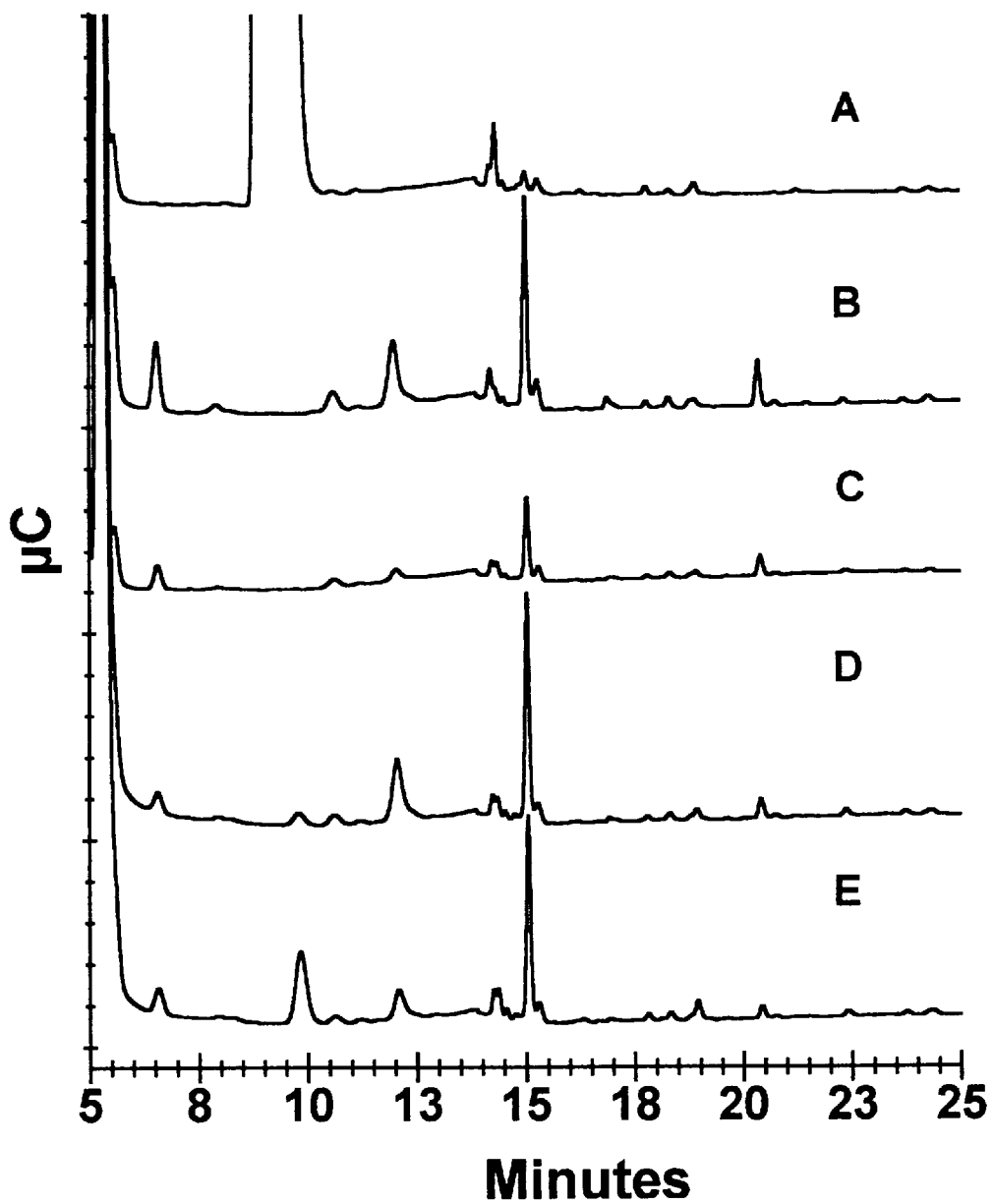
FIG. 8 shows the effect on the carbohydrate profile of incubating drought stressed (non-irrigated) cotton fibers (harvested according to the method of the invention) with a number of different added substrates: A) control-boiled to destroy enzymes; B) inositol added; C) glycerol added; D) sucrose added; and E) inositol, glycerol, sucrose and arabinose added.

FIG. 7 shows a series supernatants incubated with fibers from irrigated plants. In these experiments a known concentration of substrate (25 mM inositol, 25 mM glycerol, 25 mM sucrose and/or 25 mM arabinose) was incubated with a known weight of fiber. The control contains the normal fiber extract but was boiled to inactivate the enzymes; in the other cases the normal soluble carbohydrates were supplemented with the indicated substrates. Note that the different substrates produce different patterns—indicating that changes in pool size greatly affects the ultimate carbohydrate pattern. For example, addition of inositol greatly potentiates the consumption of sucrose (large peak near 10 minutes in the control). The addition of glycerol, inositol and arabinose to the sucrose results in enhanced consumption of the sucrose. FIG. 8 shows the same experiment performed with fibers from a drought stressed plant. While similar to FIG. 7, there are clearly differences. The overall level of soluble carbohydrates is lower, but sucrose is clearly consumed. Part of the difference may be that the stressed fibers have a different ratio of enzymes to dry weight than the normal fibers and these experiments were normalized by weight of fiber added. If anything the drought stressed fibers appear to metabolize almost all of the added carbohydrates into insoluble compounds. While this does not preclude there being a different ratio of the various enzymes, it certainly indicates the presence of active enzymes in the stressed material.

Acid Extractable Multimers

Figure 3:
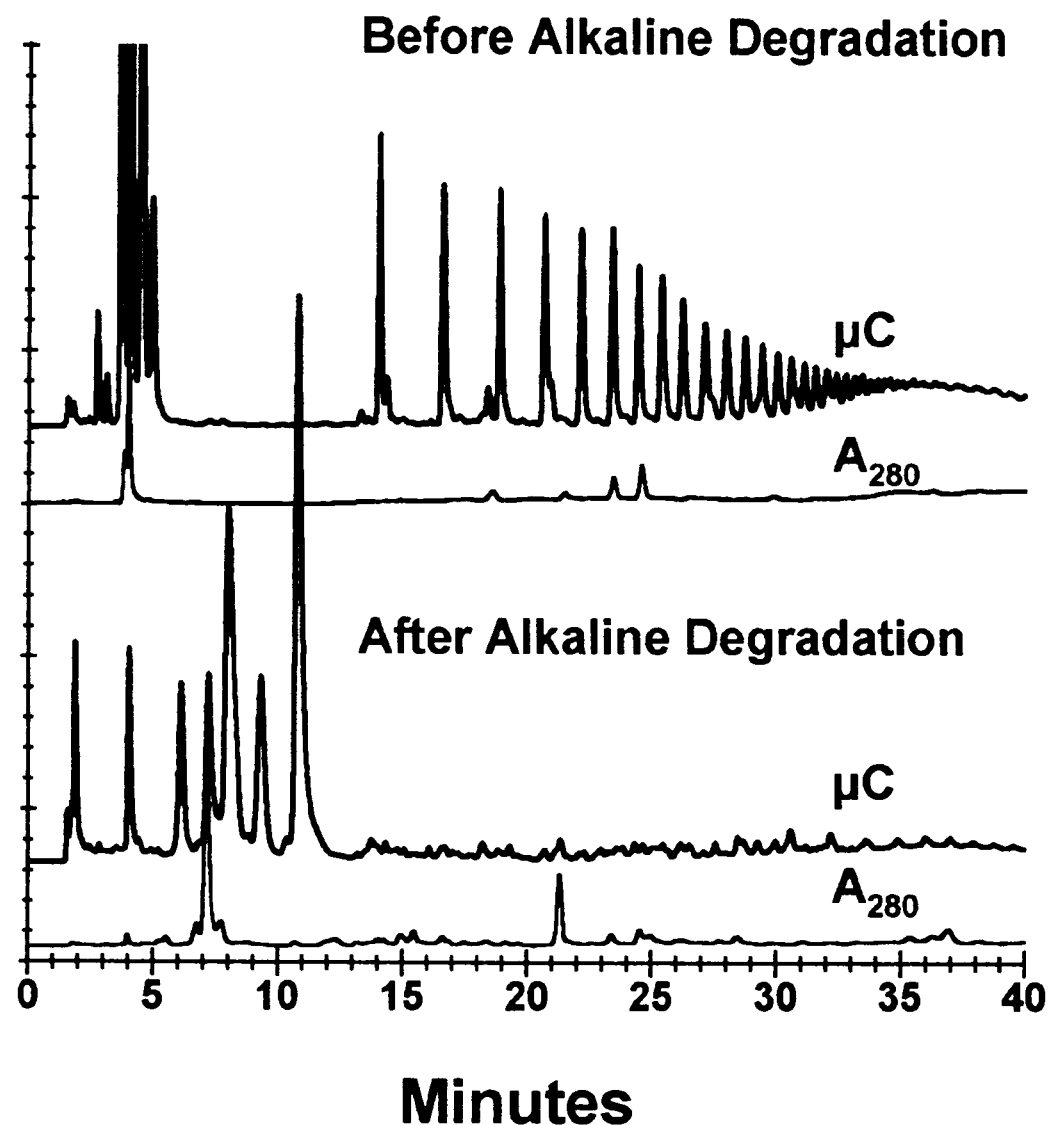
FIG. 3 shows an alkaline degradation experiment on multimers extracted from plant tissues according to the present invention.
Figure 9:
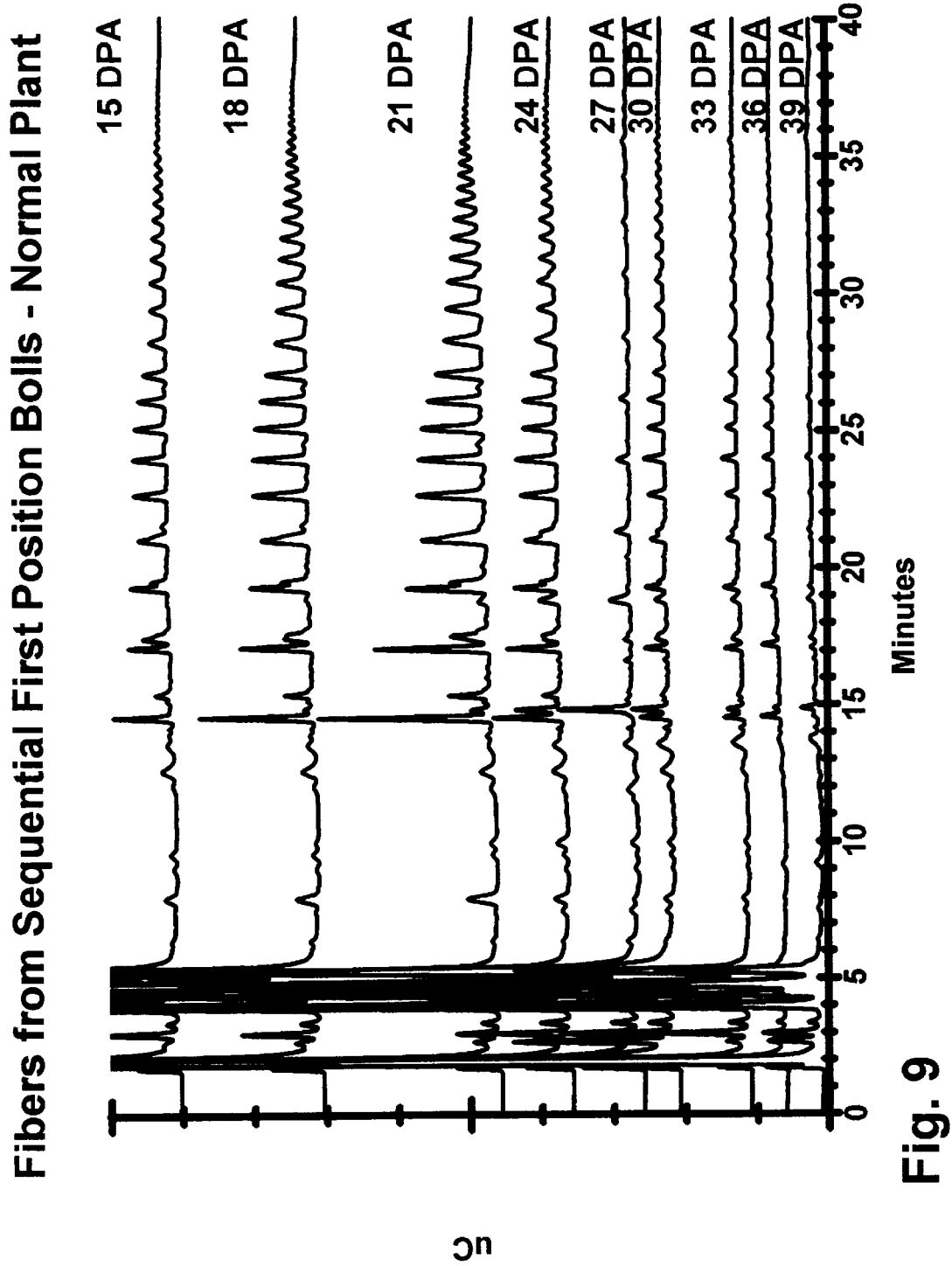
FIG. 9 shows carbohydrate multimers extracted by HCl according to the present invention from cotton fibers ranging from 15 to 39 days post anthesis; these multimers are from cotton bolls of a normally grown plant and exhibit an extremely regular periodic pattern.
Figure 10:
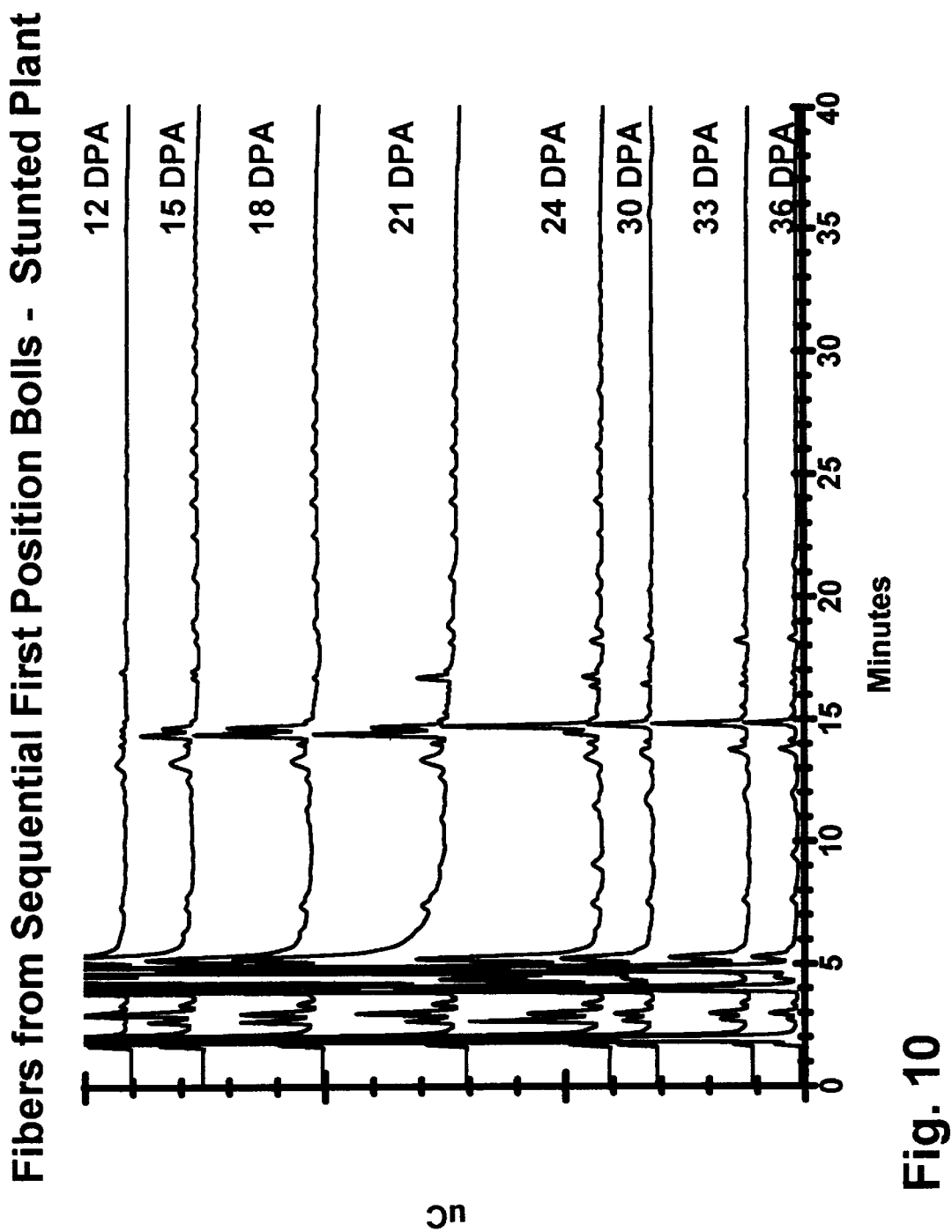
FIG. 10 shows carbohydrate multimers extracted by HCl according to the present invention from cotton fibers ranging from 12 to 36 days post anthesis; these multimers are from cotton bolls of a stunted plant growing in a portion of the field receiving suboptimal irrigation and exhibit an irregular pattern particularly between 15 and 20 minutes of retention.
Figure 11:
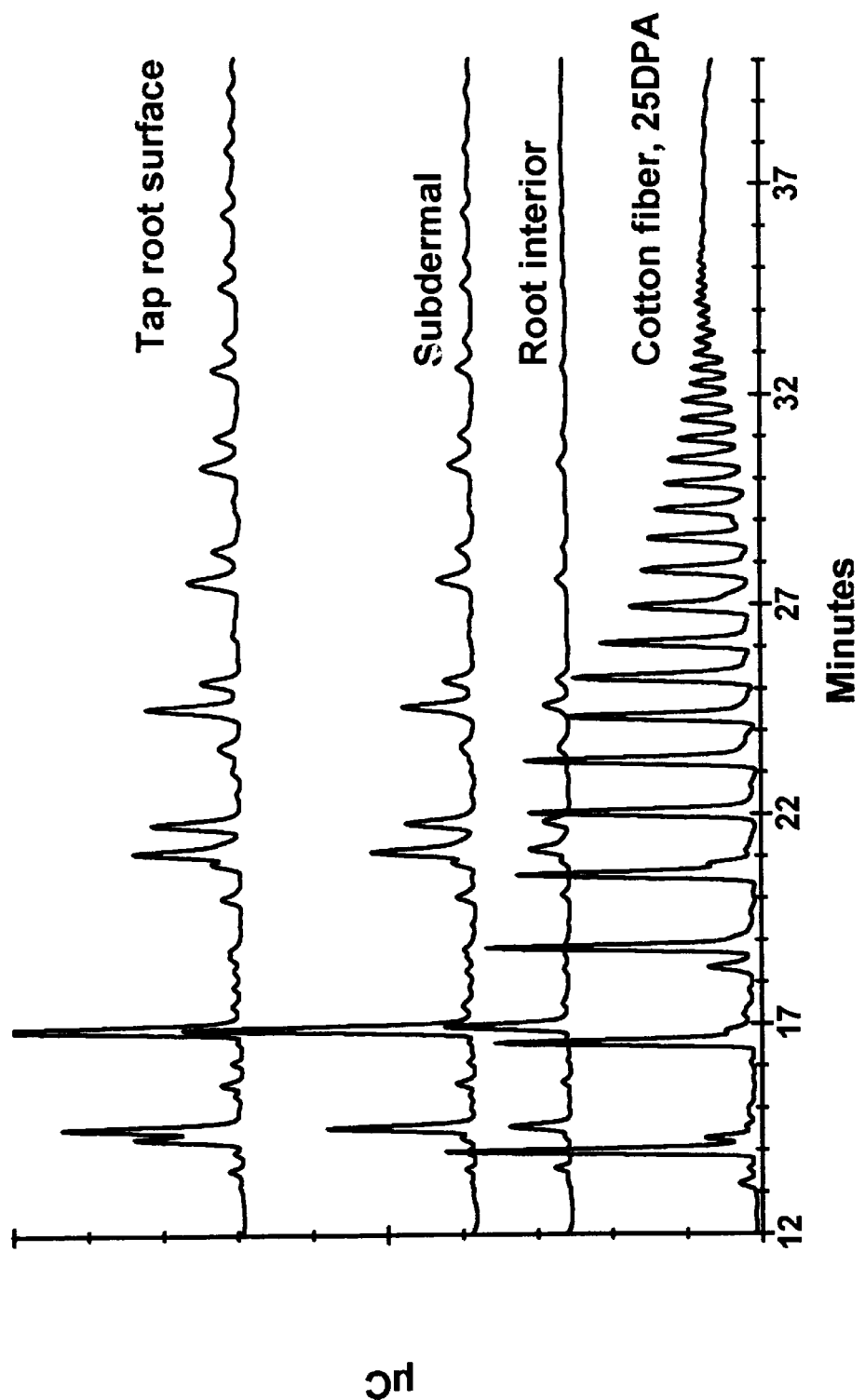
FIG. 11 compares multimers extracted from a normal cotton fiber with multimers extracted from portions of sugar beet root to demonstrate that some of these carbohydrates are found in cell walls of widely divergent plants; here the sugar beet tissue has been infected by a fungus (Rhizoctonia); the stress of infection alters the sugar beet multimers.

Perhaps the most exciting and unexpected discovery of the present research was that following the aqueous extraction it is possible to extract a multimer fraction by boiling for 30 minutes in dilute 0.1M HCl. FIG. 9 shows this unique multimer pattern extracted from cotton bolls from 15 to 39 days post anthesis. The older bolls have exactly the same multimers but in a lower per weight amount. Presumably these multimers represent some component that connects the paracrystalline cellulose in the wall. Like the GC-2 compounds the multimers are reducing sugars indicating a nontypical glycan linkage in the polymers (see FIG. 3). Hydrolysis of individual peaks has shown that they contain galactose, glucose and mannose. In classical plant cell wall research dilute mineral acids are sometime used to extract pectins or "pectic materials" which, by definition, contain galacturonic acid residues. Clearly, the multimers are not pectins or pectic materials. Further, it is necessary to first perform the cold aqueous extraction so that the multimers are not obscured by the GC-1 and GC-2 compounds. FIG. 10 shows the HCl multimers extracted from fibers on a drought stressed plant. Clearly the multimer pattern is disrupted particularly at around 15–20 minutes of retention time. The disruption of the multimer patterns is a very sensitive detector of stress and obviates the need for quantitative comparisons as is often required in making GC-1 versus GC-2 based stress detection. Further analysis of the multimers of normal fibers has revealed that the major difference between successive multimers is in addition of glucose units. That is, successive multimers in a series have comparable amounts of galactose and mannose but different amounts of glucose. It is not yet known whether the abnormal multimers of the drought stressed plants follow this pattern. It appears certain that many of these same multimers are found in a variety of cell walls. FIG. 11 shows that HCl extracts of sugar beet root tissue contains a multimer series wherein several of the compounds exactly overlap some of the cotton multimers.

Figure 12:
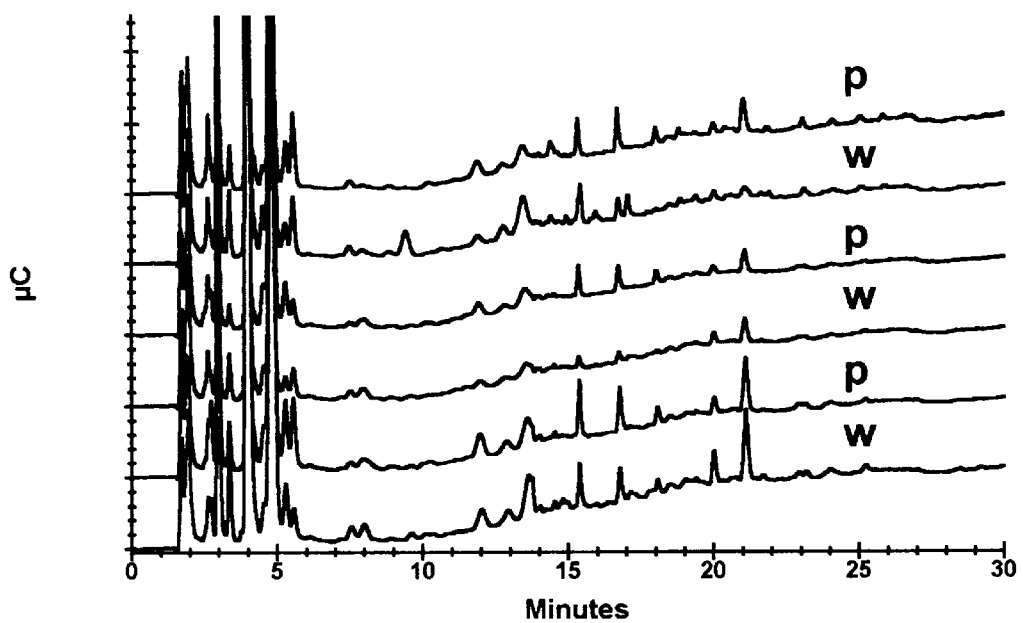
FIG. 12 shows multimers extracted from normal (p) and abnormal "white speck" (w) fibers.
Figure 13:
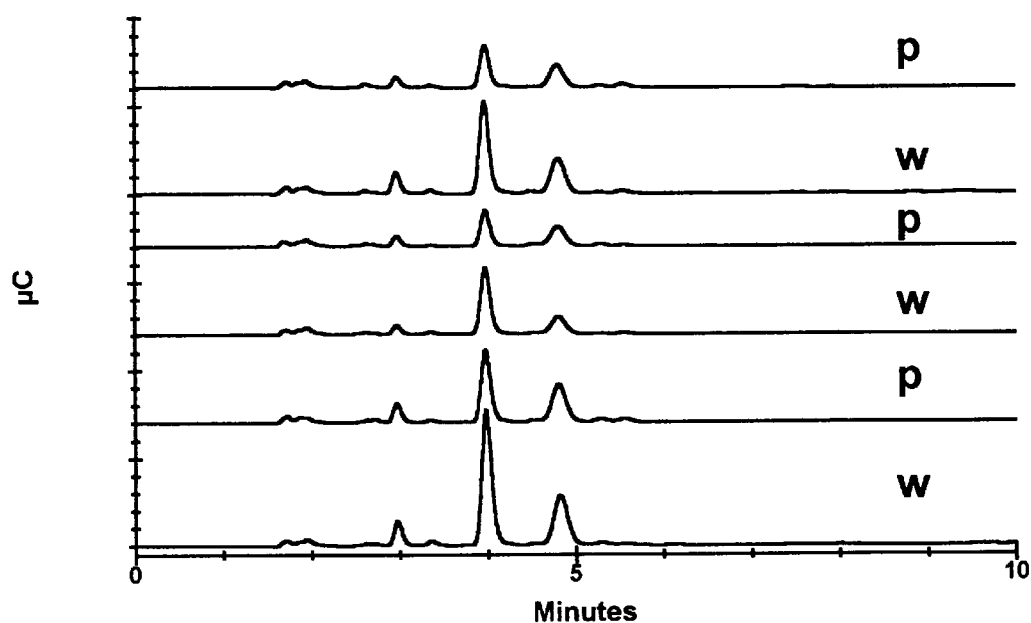
FIG. 13 shows an enlarged view of the multimer profile from FIG. 12 showing that the white speck (w) fibers have increased arabinose (ara) over the normal (p) fibers.

The multimer extraction is ideally suited for evaluating cotton fiber samples for a number of defects that plague the textile industry. Motes are immature, short fibers that lower the quality of cotton. Although their presence can be assessed by microscopic inspection of fibers, they also give a unique carbohydrate pattern allowing determination of mote contamination. Of even more importance is the presence of "white speck" fibers which are abnormal fibers that do not take up dye normally. Although this defect can be assessed by dying and inspecting the fibers, analysis of HCl multimers provides a ready way of assessing the presence of white speck fibers. As shown in FIG. 12 and FIG. 13 individual white speck (w) HCl extracts show significantly higher arabinose to glucose ratio than do the extracts (p) of normal fibers.

Figure 14:
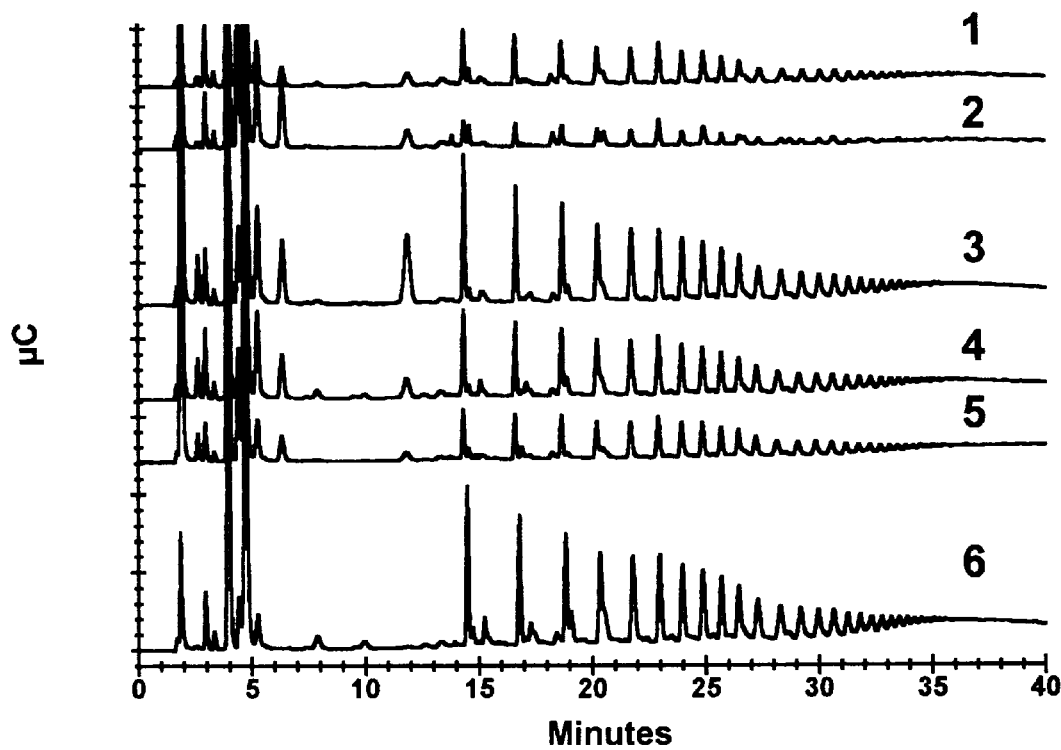
FIG. 14 shows the multimers extracted from normal fibers after incubation with a number of different substrate combinations (identified in Table 1)
Figure 14:
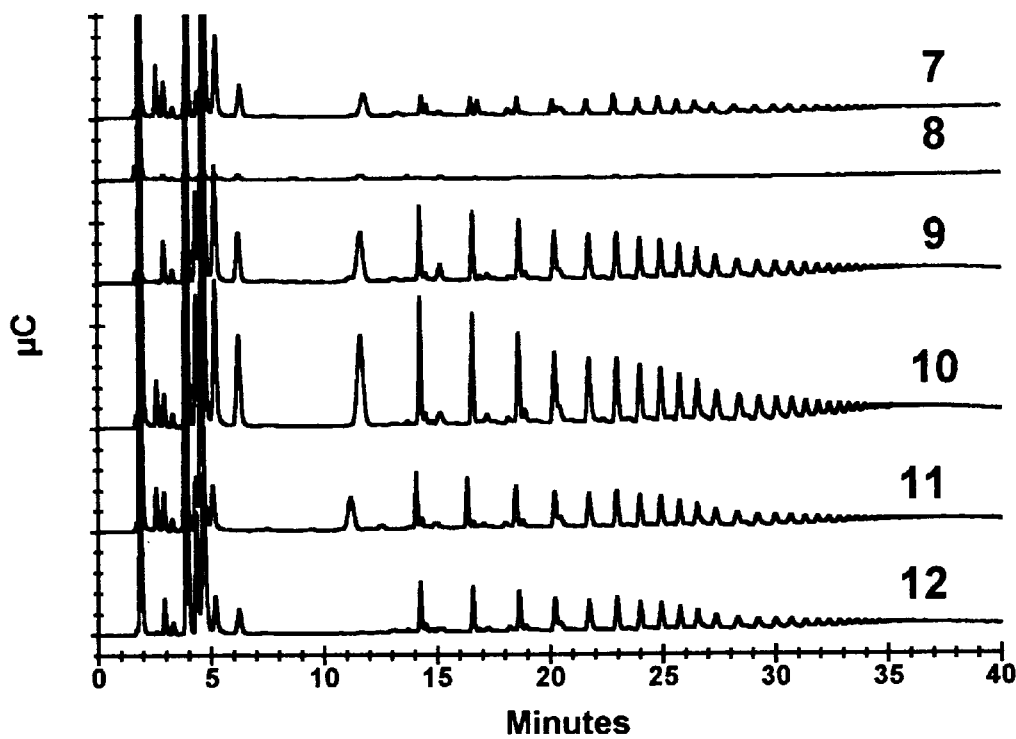

Interestingly, aqueous extracts of fibers from extremely drought stressed plants show some of the multimers. Preliminary experiments have indicated that these multimers are similar if not identical to those released by the dilute HCl treatment. The real question is why they are released by a simple aqueous treatment. One can hypothesize that the multimers are part of a hemicellulosic "glue" that holds the cell wall cellulose microfibrils together. Under drought stress conditions carbohydrate shortages and/or enzymatic defects prevent the proper assembly of the cell wall components. In such a case the "glue" does not stick properly and is very easily washed out of the walls. As will be demonstrated below, there are proteins associated with at least some of the multimers (producing a special glycoconjugate). These proteins may well be responsible to producing some of the linkages that hold the multimers into the wall. Certainly, the mild HCl extraction would be adequate to partially denature the proteins and negate their purported binding. FIG. 14 shows the multimers extracted from fibers incubated with the substrates shown in Table 1. The number associated with the particular trace relates to the substrates added. The important point is that the addition of certain substrate combinations (note traces 2 and 8, for example) appear to reduce the extraction of multimers. The control (addition of no exogenous substrates) indicates the normal extractability of the multimers. Presumably certain substrate combination produce a more tightly cross-linked product so that very few multimers can be readily extracted.

TABLE 1

| Trace # | Glycerol | Sucrose | Raffinose | Cellobiose | Inositol |
|---|---|---|---|---|---|
| 1 | 50 mM | 100 mM | 50 mM | 50 mM | 50 mM |
| 2 | 50 mM | 100 mM | 100 mM | 50 mM | 50 mM |
| 3 | 50 mM | 100 mM | 50 mM | 50 mM | 50 mM |
| 4 | 50 mM | 0 | 50 mM | 50 mM | 50 mM |
| 5 | 50 mM | 0 | 50 mM | 100 mM | 100 mM |
| 6 | 0 | 0 | 0 | 0 | 0 |
| 7 | 50 mM | 100 mM | 50 mM | 100 mM | 0 |
| 8 | 0 | 100 mM | 50 mM | 100 mM | 50 mM |
| 9 | 0 | 100 mM | 50 mM | 100 mM | 0 |
| 10 | 50 mM | 100 mM | 0 | 100 mM | 100 mM |
| 11 | 50 mM | 100 mM | 100 mM | 100 mM | 50 mM |
| 12 | 50 mM | 100 mM | 0 | 0 | 50 mM |

Figure 15:
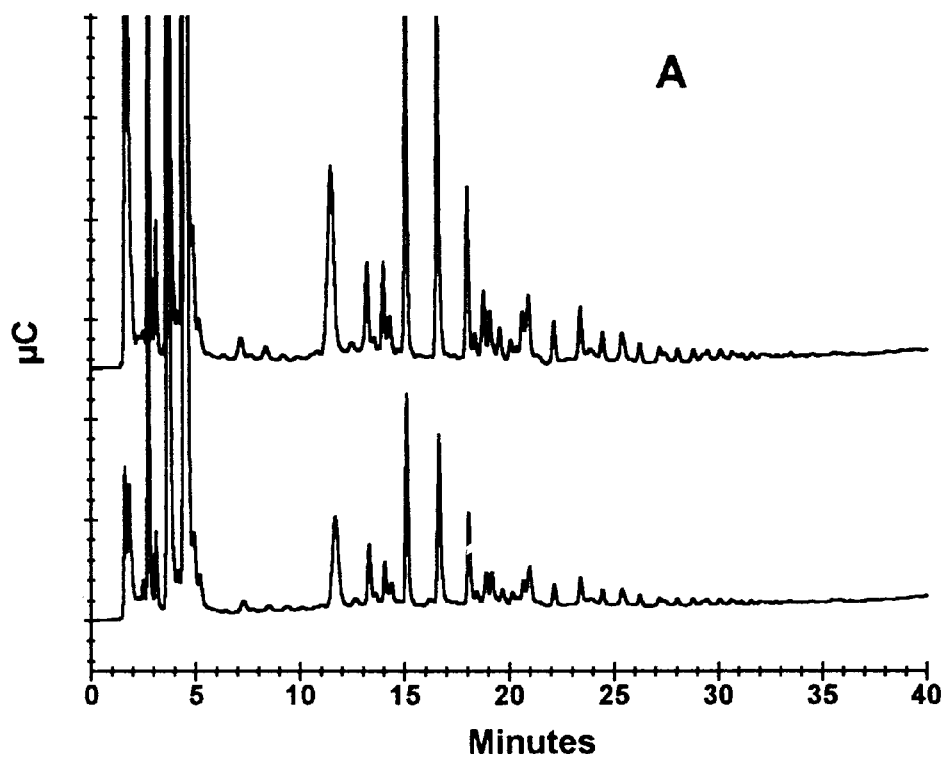
FIG. 15 shows the multimers extracted from an undyed (A) and dyed (B) cotton towel; in each case the top trace is an extract of the new towel and the bottom trace is an extract after one laundering.
Figure 15:
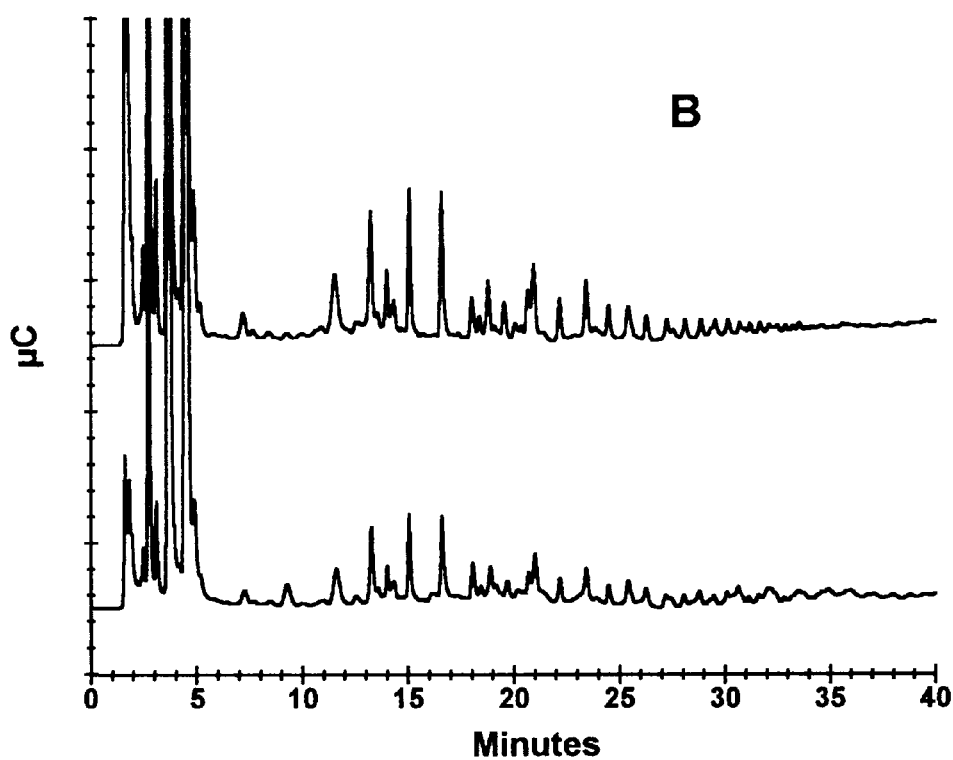
Figure 16:
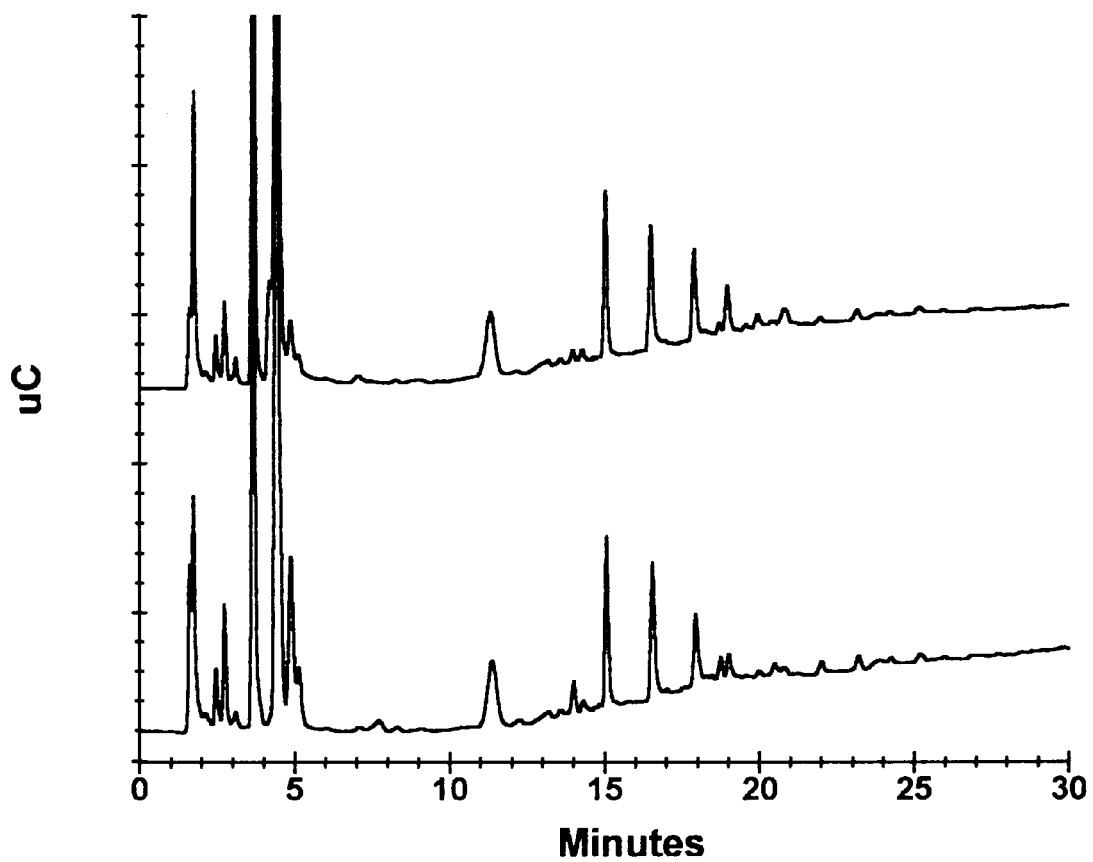
FIG. 16 shows multimers extracted from an old, much laundered pillowcase (top) and towel (bottom)
Figure 17:
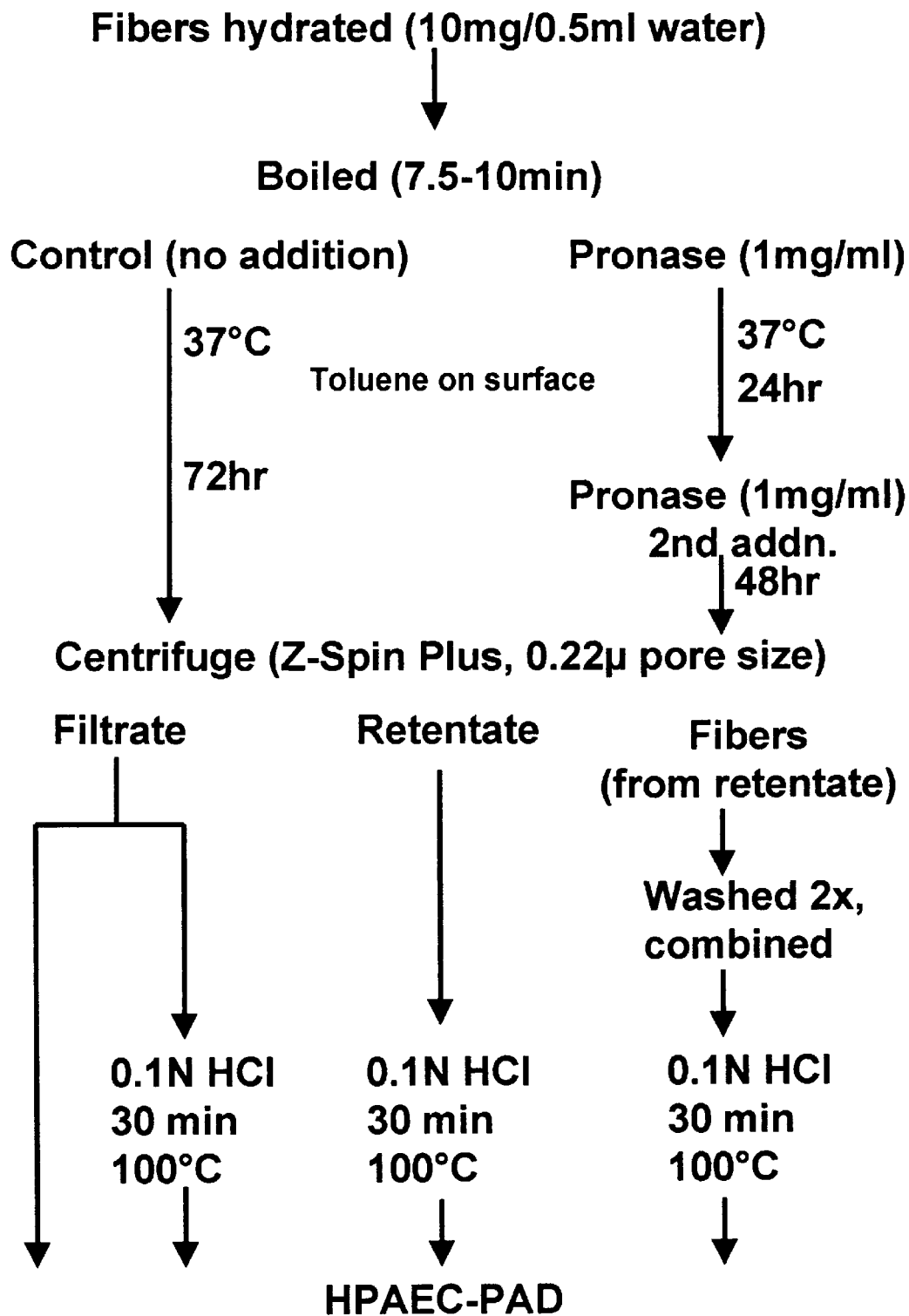
FIG. 17 shows a flow diagram for a proteolytic enzyme experiment with early, midday and late cotton fibers.

Another surprising finding is that multimers can be extracted from finished cotton fabric as well as from carefully harvested fibers as was shown above. FIG. 15 shows multimers extracted by 30 minutes of boiling in 0.1M HCl from an undyed (off white or ivory) cotton towel and from a dyed cotton towel (green). In each case the top trace represents extraction of a new towel and the second (lower) trace shows extraction of a towel that had been laundered one time. Attempts were made to standardize the amount of extracted fabric. Note that the extracted multimers look very similar to those extracted from specially prepared fibers. In this case processing of the fabric has removed all GC-1 and GC-2 compounds so that an aqueous preextraction is unnecessary—there is no danger that the GC compounds might obscure the multimers. The differences in quality and quantity of multimers extracted is due either to differences in the starting cotton or the textile processing between the two different fabrics. Experiments with "permanent press" treated cotton indicates that such treatments significantly alter the quantity and quality of extracted multimers. Another important discovery is that cotton fabrics are capable of yielding multimers even after prolonged wear and washing. FIG. 16 shows multimers extracted from an old towel and an old pillowcase in the inventors household. These fabrics had been washed dozens of times and still produced similar multimers. Clearly, the multimer analysis can be used to measure wear-related changes in cotton fabrics and to analyze various fabric treatments for their long-term effects on fabric wear. Any treatment that inhibits the release of the multimers will probably extend the lifetime of the fabric. Although a dilute acid wash is the preferred way of extracting multimers for analysis, it has been discovered that prolonged (several days) aqueous extraction at elevated temperatures also releases the multimers. Presumably long exposure to hot water gradually hydrates paracrystalline portions of the cell wall and allows the multimers to be released. This strongly suggests that these materials are gradually released during washing; undoubtedly the loss of these "glue" elements results in a weakening of the fabric. Traditionally it was believed that fabric weakening with age was merely a mechanical effect of wear and washing. These discoveries suggest that washing actually removes a vital binding component from the cotton. Treatments that slow this removal will extend the life of the cotton fabric. Another practical use of multimer extraction is the determination of cotton types used in a given fabric. Extraction of a range of different cotton varieties has shown reproducible multimere differences between some varieties. In particular certain high grade cottons are derived from different cotton species. It might be very beneficial to have a simple test to detect adulteration of these premium cottons with less expensive "ordinary" cottons.

Protein Glue and the Multimers

Figure 18:
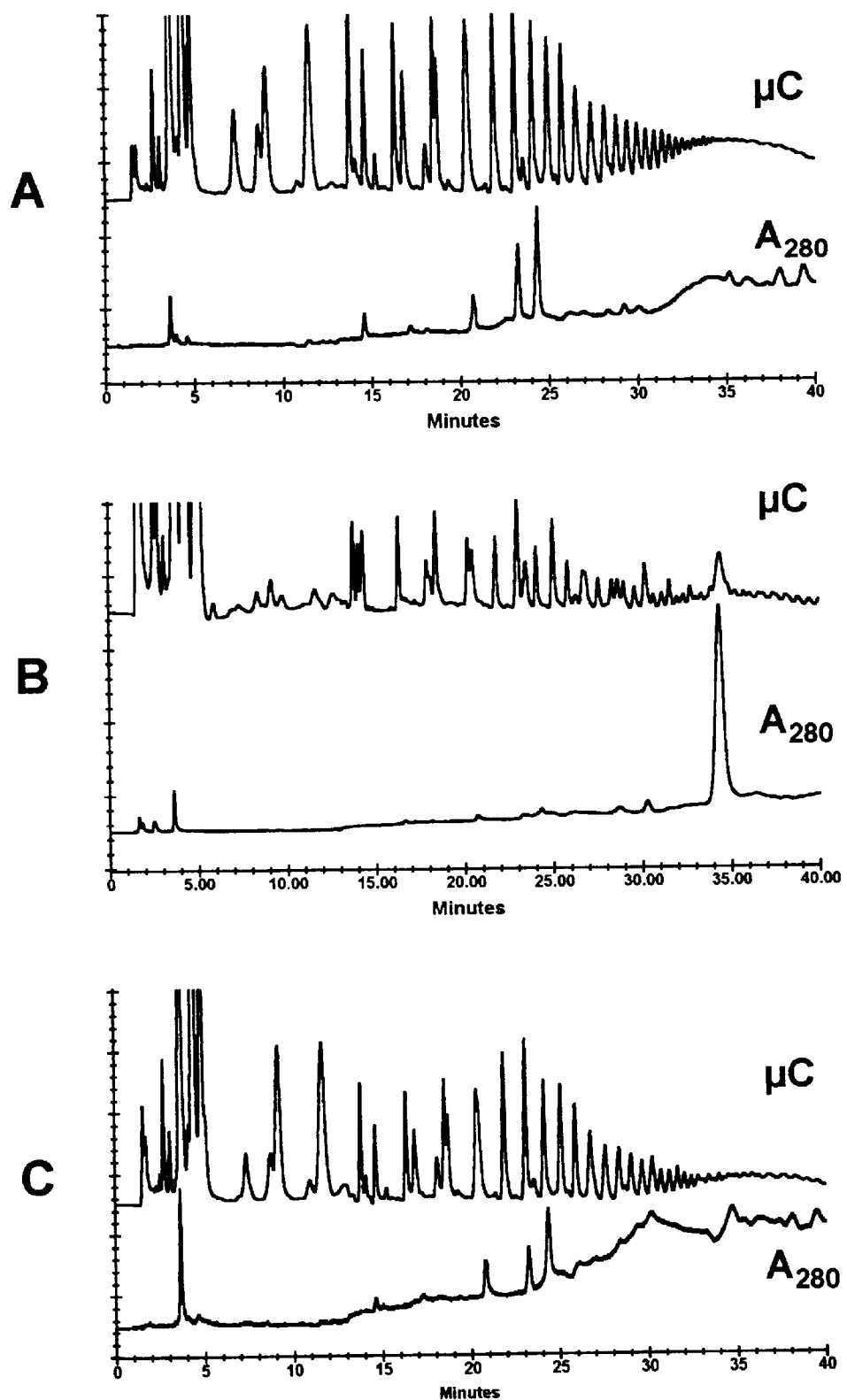
FIG. 18 shows the multimers extracted using the scheme of FIG. 17 for early (A), midday (B) and late C) fibers; besides the carbohydrate multimers, protein is also shown ($A_{280}$)

FIG. 18 shows the flow diagram of an experiment intended to determine what part, if any, protein plays in the cell wall phenomena discussed above. Fibers were hydrated and then boiled to denature any enzymes and kill any microorganisms (toluene was also added to additionally insure sterility). The fibers were then incubated at 37° C. for 72 hrs either with or without proteolytic enzyme (pronase 1 mg/ml). At the end of this time the fibers were separated from the supernatant by centrifugation. The supernatant was then passed through a 0.22 μm pore filter to remove any particulate material (this is standard procedure to protect the chromatographic columns). Surprisingly, the supernatants that were not treated with pronase plugged the filters and remained on the filter surface as a gooey material (retentate). The amount of this material depended strongly on the time of day that the source fibers were isolated. The early (7 am) fibers showed a maximum amount of this material; those from noon fibers showed an intermediate amount; while those from the late (7 pm) fibers showed a minimum amount. It is believed that this gooey retentate represents the "glue" that holds the cellulose in the cell wall. Obviously, rates of cell wall synthesis vary with time of day, and the rate of synthesis might affect the extractability of the glue material. If the filtrate (primarily from the pronase-treated samples) is treated with HCl, a typical multimer pattern is generated. Significantly, if the retentate is treated with HCl, or with proteolytic enzyme multimers are generated. This indicates that long-term aqueous extraction removes a cell wall component that includes the multimers. This material is macromolecular and forms a gooey gel. If the material is treated with proteolytic enzyme, the gel is destroyed and the multimers become soluble. The fact that this gel is held together by bonds sensitive to proteolytic enzyme strongly suggests that proteins are important is gluing the cell wall together.

Figure 19:
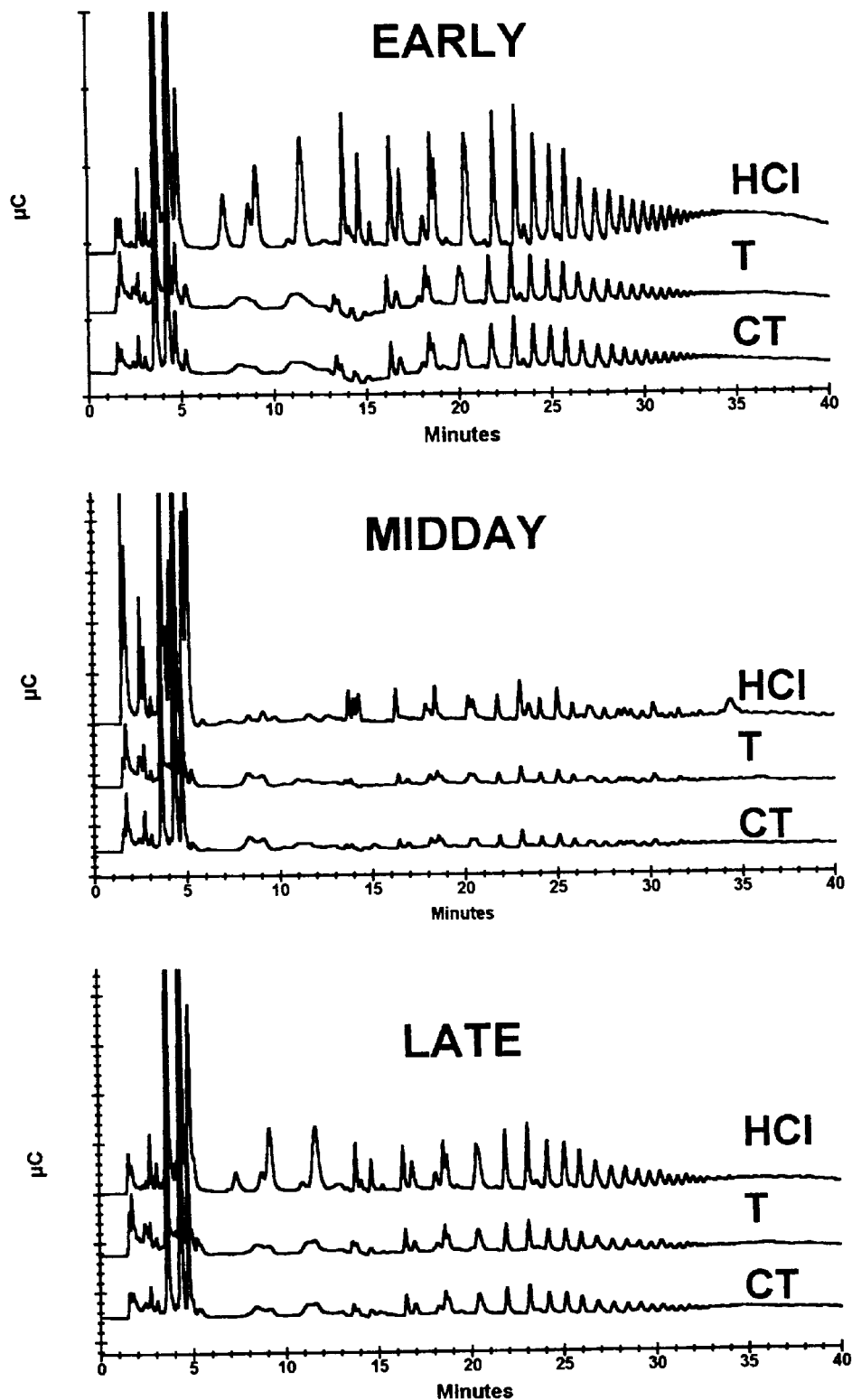
FIG. 19 shows the three multimer extracts of FIG. 18 treated with protease: trypsin (T), chymotrypsin (CT) or no protease control C).

FIG. 19 shows the multimers produced from the HCl-treated retentate of the early (top graph), midday (middle) and late (bottom)fibers. Each graph shows carbohydrates and protein ($A_{280}$). Note that certain of the multimers are clearly associated with proteins. Further, the precise nature of the proteins changes with time of day. The early and late graphs show a protein triplet peak between 20 and 25 minutes while the midday graph shows a prominent protein peak at about 35 minutes. As shown in FIG. 20, treatment of the samples with either high purity trypsin or high purity chymotrypsin removes the protein components and causes the joint protein/carbohydrate peaks to either disappear or change in shape or position.

Many alterations and modifications may be made by those having ordinary skill in the art without departing from the spirit and scope of the present invention. The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A method for monitoring growth stress in plant material comprising:

freezing and lyophilizing the plant material;

making a cold aqueous extract of the plant materials;

re-extracting the previously extracted plant materials with dilute boiling hydrochloric acid; and analyzing the hydrochloric acid extract to reveal a series of carbohydrate multimers, the pattern of multimers revealing the presence or absence of growth stress.

* * * * *